United States Patent [19]

Neperud

[11] Patent Number: 4,855,335
[45] Date of Patent: Aug. 8, 1989

[54] MEDICAL MOISTURE RESISTANT ADHESIVE COMPOSITION FOR USE IN THE PRESENCE OF MOISTURE

[75] Inventor: Michael A. Neperud, Milwaukee, Wis.

[73] Assignees: Findley Adhesives Inc., Milwaukee, Wis.; North Coast Adhesives Inc., Akron, Ohio ; a part interest

[21] Appl. No.: 146,250

[22] Filed: Jan. 20, 1988

Related U.S. Application Data

[63] Continuation-in-part of Ser. No. 910,705, Sep. 23, 1986, abandoned.

[51] Int. Cl.⁴ .......................... C08L 15/00; C08J 23/00
[52] U.S. Cl. .................................... 523/111; 524/271; 524/505
[58] Field of Search .................. 523/111; 524/271, 77, 524/505

[56] References Cited

U.S. PATENT DOCUMENTS 3,339,546  9/1967  Chen .
3,660,323  5/1972  Raguse .
3,862,068  1/1975  Russell .
3,972,328  8/1976  Chen .
4,166,051  8/1979  Cilento et al. .
4,192,785  3/1980  Chen et al. .
4,231,369  11/1980  Sorensen et al. .
4,367,732  1/1983  Poulsen et al. .
4,378,018  3/1983  Alexander et al. .
4,393,080  7/1983  Pawelchak et al. .
4,477,325  10/1984  Osburn .
4,551,490  11/1985  Doyle et al. .

Primary Examiner—Harold D. Anderson
Assistant Examiner—Dennis R. Daley
Attorney, Agent, or Firm—Quarles & Brady

[57] ABSTRACT

Adhesive compositions useful for use with medical devices, such as adhesive tapes, consist essentially of a homogeneous mixture of one or more polyisobutylenes or blends of one or more polyisobutylenes; a tackifying resin; a styrene copolymer; mineral oil; a water insoluble, water swellable, synthetic hydrocolloid which forms a gel when wet; and, an ethylene vinyl acetate copolymer which increases the dimensional stability of the final composition.

7 Claims, No Drawings

MEDICAL MOISTURE RESISTANT ADHESIVE COMPOSITION FOR USE IN THE PRESENCE OF MOISTURE

RELATED CASE

This application is a continuation-in-part of my earlier copending application Ser. No. 910,705 filed Sept. 23, 1986, now abandoned.

FIELD OF THE INVENTION

The present invention relates to adhesive compositions. More particularly, it relates to adhesive compositions which will adhere to moist body surfaces and are suitable for medical use.

BACKGROUND OF THE INVENTION

The patent literature discloses various adhesive compositions containing hydrocolloids for use in medical applications in which an adhesive which adheres to moist body surfaces is required.

In the Chen U.S. Pat. No. 3,339,545 an adhesive composition is disclosed which comprises a blend of one or more water soluble or water swellable hydrocolloids and a viscous substance such as polyisobutylene.

In the Chen U.S. Pat. No. 3,972,328 surgical bandages are disclosed which comprise an adhesive layer containing a hydrocolloid, a layer of flexible semi-open cell foam and an outer water impervious layer.

In the Chen et al. U.S. Pat. No. 4,192,785 an adhesive composition is described as suitable for use with an ostomy appliance. It consists of a mixture of one or more hydrocolloid gums, a pressure sensitive adhesive, such as one or more polyisobutylenes, and a cohesive strengthening agent. The cohesive strengthening agent can be a natural or synthethic fibrous material, finely divided cellulose, crosslinked dextran, cross-linked carboxymethylcellulose, or a starch-acrylonitrile graft copolymer.

In the Celento et al. U.S. Pat. No. 4,166,051 a putty-like adhesive composition is disclosed for use around a estoma. It consists of a homogeneous mixture of a pressure sensitive adhesive component such as polyisobutylene, mineral oil, and hydrocolloid gums or cohesive strengthening agents or mixtures thereof.

In the Pawelchak et al. U.S. Pat. No. 4,393,080 adhesive compositions for medical use are disclosed which comprise a homogeneous mixture of polyisobutylenes and one or more natural of synthetic polymers capable of developing elastomeric properties when hydyrated such as gluten and long chain polymers of methyl vinyl ether/maleic acid. The composition may also include one or more water soluble hydrocolloid gums and may additionally contain one or more water swellable cohesive strengthening agents. Additionally, one or more thermoplastic elastomers such as styrene copolymers and small amounts of mineral oil may be included within the composition.

In the Sorensen et al. U.S. Pat. No. 4,231,369 an ostomy skin barrier is disclosed consisting of a styrene copolymer having dispersed therein a water soluble hydrocolloid gum and a tackifier.

In the Poulsen et al. U.S. Pat. No. 4,367,732 there is disclosed an ostomy skin barrier consisting of a water soluble hydrocolloid dispersed in a continuous phase consisting of a styrene copolymer, a hydrocarbon tackifier, a plasticizer, an antioxidant, and an oily extender.

In the Alexander et al. U.S. Pat. No. 4,378,018 there is disclosed an adhesive composition for use with a male incontinence device comprising a mixture of hydrocolloid, polyhydroxy alcohol, fumed silica, and polyacrylamide.

Finally, in the Doyle et al. U.S. Pat. No. 4,551,490 there are disclosed medical grade pressure sensitive adhesive compositions comprising a homogeneous mixture of one or more polyisobutylenes or blends of one or more polyisobutylenes and butyl rubber, one or more styrene radial or block type copolymers, mineral oil, one or more water soluble hydrocolloid gums, and a tackifier. One or more water swellable cohesive strengthening agents, an antioxidant, and various other optional ingredients also may be included within the adhesive composition.

The above described patented adhesives are improvements over previously available adhesives but a need still exists for better adhesive compositions which will adhere to moist body surfaces and which are suitable for medical use.

BRIEF SUMMARY OF THE INVENTION

The present invention relates to novel pressure sensitive adhesive compositions particularly adapted for medical use.

It is the primary object of the present invention to disclose adhesive compositions which possess superior ability to adhere to moist body surfaces and which resist degradation in the presence of moisture and are non-irritating to human skin.

The adhesive compositions of the present invention are a homogeneous blend of mineral oil, a tackifying resin, one or more polyisobutylenes or mixtures of one or more polyisobutylenes, a water swellable hydrocolloid, a styrene copolymer, an ethylene vinyl acetate copolymer and various other optional ingredients such as water soluble gums, natural gums, antioxidants and preservatives.

These pressure sensitive adhesive compositions can be used in a wide variety of medical applications because they are resistant to degradation by moisture, including biological fluids, and are non-irritating to the human skin.

The pressure sensitive adhesive compositions of this invention can be used to adhere devices to body tissue or combined with other materials, such as plastic films, to form adhesive strips which can be used to hold an incontinence device or wound drainage device in place or to provide a skin barrier or an adhesive faceplate of a drainable ostomy pouch. These adhesive compositions are especially adapted for use in the surgical bandages of the type shown in the Chen U.S. Pat. No. 3,972,328.

DETAILED DESCRIPTION OF THE PREFERRED EMBODIMENT OF THE INVENTION

The pressure sensitive adhesive compositions of the preferred embodiment are a homogeneous blend of about 12% to about 20% mineral oil, about 30% to about 40% of a tackifying resin, about 15% to about 30% of a water insoluble, water swellable, synthetic hydrocolloid, about 5% to about 10% of one or more polyisobutylenes or mixture of one or more polyisobutylenes, about 7% to about 15% of a styrene copolymer, and about 1% to about 8% of an ethylene vinyl acetate copolymer in which all percentages are by weight of the final composition. The compositions may also contain other ingredients including stabilizers, antioxidants, water swellable cohesive strengthening agents, and the like. If a proper mixture of ingredients is used, compositions can be tailored to have a desired balance of adhesion, durability and elasticity.

The polyisobutylenes employed preferably are one or more low molecular weight polyisobutylenes having a viscosity average molecular weight of from about 40,000 to about 58,000 (Florey). Especially preferred is the polyisobutylene commercially available under the trademark Vistanex LMMS from Exxon. The polyisobutylene is present in amounts ranging from about 5% to about 10% by weight of the composition. The polyisobutylene provides dry tack or adhesion to dry body surfaces and improves conformability.

The preferred styrene copolymer of the adhesive compositions include styrene-butadiene-styrene (S-B-S) and styrene-isoprene-styrene (S-I-S) block type copolymers both of which are commercially available, for example, from Shell Chemical Co. under the tradename Kraton as Kraton 1100, 1101, 1102, 1107, etc. Especially preferred is the styrene-isoprene-styrene (S-I-S) block type copolymer Kraton 1107. The styrene copolymer is present in an amount of from about 7% to about 15% by weight of the composition. The styrene copolymer functions to provide extensibility and both rapid and complete recovery from modular strains to the composition.

The term "block" copolymer is meant to denote polymeric chains containing alternating blocks of polymers, each block differing materially from the next adjacent block. Examples of block copolymers applicable to the present invention include: Shell's Kraton 1101 and Kraton 1102 (A=polystyrene and B=1,4 polybutadiene), Kraton 1107 (A=polystyrene and B=polyisoprene), Kraton G (A=polystyrene and B=polyethylene-propylene copolymer), Dow Corning X4-2516 lot 114 (A=polyalphamethylstyrene and B=polydiamethylsiloxane) Firestone's Stereon 840 (A=polystyrene and B=polyisobutadiene), and AMOCO's Resin 18 (A=polystyrene and B=polyisoprene). The development of block copolymers or thermoplastic elastomers is an active field with new materials being continually introduced.

The above unvulcanized block copolymers have individual chains consisting of three or more blocks, the elastomeric intermediate block, and a thermoplastic block on each end. Since the end blocks and the elastomeric intermediate blocks are mutually incompatible, the bulk polymer separates into two microphase regions, the block A phase and the block B phase. Where the thermoplastic end blocks are in minor proportions, as employed in the present invention and as noted more fully below, such end blocks associate together to form discrete particles, such particles acting as crosslinks for the elastomeric intermediate block. The resulting network is thus held together by reversible physical bonds in contrast to the permanent chemical bonds characteristic of vulcanized or cured elastomers. Under these conditions, the end blocks coalesce when cast from a solvent or congeal when cooled from a melt to form sub-microscopic particles. The particles, held together by van der Waals forces, form a discrete phase while the elastomeric mid-blocks form a continuous phase. Each individual molecule thus has its end blocks in one of the many particles and its intermediate block in the continuous elastomer phase.

For purposes of the present invention, the minimum average molecular weight of each end block is about 5,000, the average molecular weight of each such end block ranging from about 5,000 to about 50,000, so that the minimum total average molecular weight of both end blocks is about 10,000, the total average molecular weight of both end blocks ranging from about 10,000 to about 100,000. The minimum average molecular weight of the intermediate or mid-block is about 25,000, the average molecular weight of such intermediate block ranging from about 25,000 to about 500,000, the preferred average molecular weight range of such intermediate block ranging from about 25,000 to about 200,000.

In one preferred embodiment, the non-elastomeric thermoplastic end blocks are styrene and the elastomeric polymer intermediate block is selected from the group consisting of butadiene and isoprene polymer blocks. Such styrene-butadiene and styrene-isoprene block copolymers and their method of preparations are described U.S. Pat. No. 3,265,765. Specific examples of such block copolymers which can be employed in producing the elastomer composition of the invention are the thermoplastic rubber copolymers marketed as Kraton 1107 which is a styrene-isoprene block copolymer, each polystyrene end block of which has an approximate average molecular weight of about 8,000 to 12,000. The polyisoprene intermediate block has an average molecular weight of about 34,000 to 60,000, total average molecular weight of Kraton 1107 copolymer being about 50,000 to 84,000. The Kraton 1107 block copolymer is marketed by Shell Chemical Company.

The mineral oil is included within the pressure sensitive adhesive composition to increase the aggressiveness of the bonding without requiring undue pressure in applying the adhesive composition to the body, i.e., "wet grab". The mineral oil also functions to increase the stretchability of the final composition. The mineral oil is present in the adhesive compositions of this at from about 12% to about 20% by weight of the final composition.

The tackifying resin employed in the compositions increases tack. The preferred resins are the glycerol esters of highly hydrogenated resin. Especially preferred is the product sold under the trade name FORAL 85 by Hercules Inc. The tackifying resin is present in an amount ranging from about 30 to about 40 parts per 100 of the final composition.

The tackifying resin component which is used in the adhesive of the present invention appears to extend the adhesive properties of the block polymer. As used herein, the term "tackifyingresin" includes: (a) natural and modified rosins such, for example, as gum rosin, wood rosin, tall-oil rosin, distilled rosin, hydrogenated rosin, dimerized rosin, and polymerized rosin; (b) glycerol and pentaerythritol esters of natural and modified rosins, such, for example, as in the gycerol ester of pale wood rosin, the glycerol ester of hydrogenated rosin, the glycerol ester of polymerized rosin, the pentaerythritol ester of hydrogenated rosin, and the phenolic modified pentaerythritol ester of rosin; polyterpene resins having a softening point, as determined by ASTM method E28 58T, of from about 60° to 140° C., the latter polyterpene resins generally resulting from the polymerization of terpene hydrocarbons, such as the bicyclic mono-terpene known as pinene, in the presence of Friedel-Crafts catalysts at moderately low temperatures; (d) phenolic-modified terpene resins such, for example, as the resin product resulting from the condensation in an acidic medium, of a bicyclic terpene and a phenol; and (e) aliphatic petroleum hydrocarbon resins having a Ball and Ring softening point of from about 60° to 140° C., the latter resins resulting from the polymerization of monomers consisting primarily of olefins and diolefins. Especially preferred is a polymerized tall oil rosin available under the name SYLVATAC 95 from Sylvachem Corporation of Jacksonville, Florida.

The water insoluble, water swellable synthetic hydrocolloid included within the preferred pressure sensitive compositions is a polyacrylic acid metallic salt which can absorb up to 850 times its weight in liquid and which turns into a gel when wet so that liquids are contained without leakage. The water swellable hydrocolloid enables the adhesive compositions to adhere to moist body surfaces, i.e., wet tack. Especially preferred as the hydrocolloid ingredient is the product sold under the tradename Arasorb 720F by Arakawa chemical (USA) Inc., Chicago, Ill. The hydrocolloid is preferrably present in about 15% to about 30% by weight of the final composition. Other hydrocolloids, including hydrolyzed starch polyacrylonitrite graft copolymer metallic salts, can be used but offer no apparent advantages and may not be as heat stable.

The ethylene vinyl acetate copolymers are present as about 1% to about 8% of the composition by weight and they enhance moisture absorbency and resistance and increase dimensional stability. The ethylene/vinyl acetate component of the adhesive of the present invention is known in the art, especially as a resin for blending in hot-melt coatings and adhesives.

Several manufacturers produce these copolymers. The Plastic Products and Resins Department of the DuPont Company produces a large number of composition and viscosity combinations under their general trademark "Elvax (R)." The Elvax resins are sold in "grade" groupings based on vinyl acetate content: for example, 200-series resins contain about 28 percent vinyl acetate; 300-series, 25 percent; and 400 series, 18 percent. Within each series the inherent viscosity rises with increasing grade number, from 0.54 with Elvax 210, to 0.94 with Elvax 260, and 1.01 with Elvax 265. Among these resins Elvax EP170, which has a melt index of 0.7, has proved particularly effective in compositions of the present invention. All grades of Elvax are stabilized against viscosity variation in use by addition of 50–1000 ppm of butylated hydroxytoluene.

Small amounts, i.e., less than about 5% by weight of the adhesive composition, of other ingredients may be included in the adhesive composition. For example, the composition may contain about 0.5% by weight or more of an antioxidant such as a hindered phenol antioxidant or a zinc dibutyldithiocarbamate (commercially available from R. T. Vanderbilt Co. under the tradename Butyl Zimate) or those available from Ciba Geigy such as Irganox 1010, tetrakis [methylene (3,5-ditertbutyl-4-hydroxyhydrocinnamatemethane), or Irganox 1076, octadecyl 3-[3,5-ditert-butyl-4'-hydroxyphenyl]-propionate. Stabilizers such as organo phosphite stabilizers also may be included in amounts of from about 0.5% to 1.5% by weight of the final composition.

One or more water swellable cohesive strengthening agents also may be included within the pressure sensitive adhesive compositions but are generally not needed when the preferred hydrocolloid is used. The cohesive strengthening agents along with the water soluble hydrocolloid gums function to control the rate of hydration of the adhesive compositions and enable them to resist erosion by biological fluids such as urine. Suitable water soluble hydrocolloid gums include sodium carboxymethylcellulose, which is preferred, pectin, gelatin, guar gum, locust bean gum, gum karaya, and mixtures thereof. Suitable water swellable cohesive strengthening agents include finely divided substantially water insoluble cross-linked sodium carboxymethylcellulose such as that commercially available under the trademark AcDiSol or Aqualon and available commercially from Hercules Corp. or FMC or that described in U.S. Pat. No. 3,589,364, finely divided substantially water insoluble starch-acrylonitrile graft copolymer such as that described in U.S. Pat. No. 3,661,815 and commercially available from the Grain Processing Corp., and finely divided substantially water insoluble cross-linked dextran such as that commercially available under the trademark Sephadex. The preferred water swellable cohesive strengthening agent is cross-linked sodium carboxymethylcellulose.

The swellable cohesive strengthening agents may be included at about 1% to 10% by weight of the adhesive compositions.

In addition, small amounts of a pharmacologically active ingredient can be included in the adhesive composition. For example, an antibiotic or antimicrobial agent such as neomycin, an antiseptic agent such as povidone iodine, an antiinflammatory agent such as hydrocortisone or triamcinolone acetonide, or a skin protective agent such as zinc oxide. When the bandage is used as a burn dressing, small amounts of active ingredients such as silver sulfadiazine, sulfadiazine, and other silver compounds can be included in the composition. Also, small amounts, i.e., less than 1% by weight of the adhesive composition, of physical reinforcing agents for the polymeric substituents can be included such as carbon black, polyaramids (commercially available under the tradename Kevlar), hydrated silicas, etc.

The adhesive compositions of this invention are prepared by combining the polyisobutylene, tackifying resins, mineral oil, antioxidant and stabilizer with heating and agitation in a heavy duty high shear or blade type mixer. The mixture is heated from about 120° to about 160° C. and mixing is continued until the mass is homogeneous. The water swellable hydrocolloid, water soluble gums, water swellable cohesive strengthening agents, and the other optional ingredients are added with mixing at about 140° C. The styrene copolymer and the ethylene vinyl acetate copolymer are added with continued heating and mixing at about 120° to about 160° C. The resultant homogeneous mass is then extruded into suitable containers for subsequent processing by conventional hot melt coating equipment.

By further adjusting the percentage of the components of the adhesive compositions of this invention, properties such as duration of adhesion, resistance to erosion, stretchability, and removal without skin stripping can be varied according to the particular use.

The adhesive compositions of this invention may be sterilized by means of gamma radiation.

The following examples are illustrative of the invention. Other suitable adhesive compositions can be obtained by minor variations in the amounts of ingredients employed.

General Preparation

The mineral oil, tackifying resin and polyisobutylene, were combined in a blade mixer with heating (about 150° C.) and agitating for approximately 1 to 2 hours. The mixture was cooled to about 140° C. and the hydrocolloid was added. After another 15 minutes of blending, the styrene copolymer and the EVA copolymer were added. Mixing was continued at about 150° C. for 2 hours until a homogeneous mass was obtained. The mass was cooled or applied when hot to the desired substrate or backing.

Competitive A is approximately 45 mils thick and Competitive B is approximately 60 mils thick).

The test data indicates that the adhesives of the present invention are substantially more absorbent and less prone to erosion than the competitive materials which are of the type disclosed in the Doyle et al. patent.

TABLE 1

|  | Example 1 | Example 2 | Example 3 | Competitive A | Competitive B |
|---|---|---|---|---|---|
| Water Erosion test (percent weight lost) | 11.3% | 4.1% | 5.2% | 32.8% | 12.6% |
| Water Absorption Rate (grams/meter2/hour) |  |  |  |  |  |
| Average over 1st 4 hours | 3110 | 1036 | 6606 | 628 | 1096 |
| Average over 24 hours | 1964 | 1073 | 1366 | 102 | 308 |
| Adhesive mass (grams) | 0.54 g | 0.54 g | 0.54 g | 0.90 g | 1.24 g |
| Total Weight of water Absorbed over 24 hours | 30.6 g | 16.8 g | 21.3 g | 1.6 g | 7.1 g |

EXAMPLES

| Preparations | 1 | 2 | 3 |
|---|---|---|---|
| Mineral Oil | 17.61 | 15.29 | 16.76 |
| Glycerol ester of highly hydrogenated rosin (Foral 85) | 36.27 | 38.23 | 33.52 |
| Polyisobutylene (Vistanex LMMS) | 6.22 | 9.17 | 8.94 |
| Poly (acrylic acid) metallic salt (Arasorb 720F) | 25.91 | 17.58 | 27.93 |
| Styrene-isoprene-styrene block copolymer (Kraton 1107) | 8.29 | 12.23 | — |
| (Kraton 1112) | — | — | 8.94 |
| Ethylene/Vinyl-Acetate (EVA) Copolymer (Elvax EP170) | 4.14 | 6.12 | 2.23 |
| Hindered phenol antioxidant | 0.52 | 0.46 | 0.56 |
| Organo phosphite stabilizers | 1.04 | 0.92 | 1.12 |
|  | 100.00 | 100.00 | 100.00 |

Preparations 1, 2 and 3 were prepared in the manner described and used in the preparation of surgical bandages as described in the Chen U.S. Pat. No. 3,972,328. Comparative tests were performed comparing the Preparations 1, 2 and 3 with two competitive preparations A and B which do not contain EVA and are of the type disclosed in the Doyle et al. patent (supra).

The first comparative test can be described as an accelerated water erosion test. This involves taking a weighed sample, placing it in a beaker of water and agitating it for 3 hours with a magnetic stirrer. The sample is then removed and the water is filtered to extract any eroded material. The filter is dried and weighed to determine the weight of material eroded, which is divided into the initial sample weight to obtain a percent eroded. The second test is an absorption rate test which determines how much water a sample will absorb and how fast it will occur. This test involves immersing a weighed sample of adhesive in water and periodically measuring sample weight changes due to absorption. The absorption rate is reported as: grams of water absorbed/square meter of surface area/hour immersed.

The results of the test are reported in Table 1 which also contains data on the mass of adhesive tested and the total amount of water absorbed by that mass. The differences in adhesive mass are due to variations in adhesive thickness (i.e., Examples 1, 2 and 3 are 30 mils thick, It will be readily apparent to those skilled in the art that the foregoing examples have been included for purposes of illustration and that variations may be made in proportions, procedures and materials without departing from the scope of the present invention. Therefore, it is intended that the invention not be limited except by the claims which follow:

I claim:

1. A moisture resistant adhesive composition for use in the presence of moisture, said adhesive consisting essentially of a substantially homogeneous mixture one a percent weight basis of from about 5% to abut 10% of one or more low molecular weight polyisobutylenes, from about 7% to about 15% of a styrene block copolymer, from about 12% to about 20% of mineral oil, from about 15% to about 30% of a water insoluble, water swellable synthetic hydrocolloid which is a polyacrylic acid metallic sal that forms a gel when it is wet, from about 1% to about 8% of an ethylene vinyl acetate copolymer which increases dimensional stability and from about 30% to about 40% of a tackifying resin.

2. An adhesive composition of claim 1 in which in the styrene copolymer is a styrene-isoprene-styrene block copolymer.

3. An adhesive composition of claim 1 in which tackifying resin is a glycerol ester of rosin.

4. A medical device comprising in part an adhesive layer containing a moisture resistant, pressure sensitive adhesive composition consisting essentially of a substantially homogeneous mixture on a percent weight basis of form about 5% to about 10% of one or more polyisobutylenes, from about 7% to about 15% of a styrene copolymer, from about 12% to about 20% of mineral oil, from about 15% to about 30% of a water insoluble, water swellable hydrocolloid which is a polyacrylic acid metallic salt, which turns into a gel when it is wet, from about 30% to about 40% of a tackifying resin and about 1% to about 8% of an ethylene vinyl acetate copolymer which increases dimensional stability.

5. A medical device of claim 4 wherein the styrene copolymer is a styrene-isoprene-styrene block copolymer.

6. A medical device of claim 4 wherein the polyisobutylene is a low molecular weight polyisoutylene.

7. A medical device of claim 4 wherein the tackifying resin is a glycerol ester of rosin.

* * * * *

UNITED STATES PATENT AND TRADEMARK OFFICE
CERTIFICATE OF CORRECTION

PATENT NO. : 4,855,335
DATED : August 8, 1989
INVENTOR(S) : Neperud

It is certified that error appears in the above-identified patent and that said Letters Patent is hereby corrected as shown below:

| | |
|---|---|
| Column 8, line 32 | "one" should read --on-- |
| Column 8, line 33 | "abut" should read --about-- |
| Column 8, line 39 | "sal" should read --salt-- |
| Column 8, line 52 | "form" should read --from-- |
| Column 8, line 65 | "polyisoutylene" should read --polyisobutylene-- |

Signed and Sealed this

Third Day of July, 1990

*Attest:*

HARRY F. MANBECK, JR.

*Attesting Officer*　　　*Commissioner of Patents and Trademarks*